(12) United States Patent
Racine

(10) Patent No.: US 9,732,049 B2
(45) Date of Patent: Aug. 15, 2017

(54) PROCESS FOR PREPARING 2,4-DIAMINO-3-HYDROXYBUTYRIC ACID DERIVATIVES

(71) Applicant: Nosopharm, Nimes (FR)

(72) Inventor: Emilie Racine, Bouillargues (FR)

(73) Assignee: Nosopharm (FR)

( * ) Notice: Subject to any disclaimer, the term of this patent is extended or adjusted under 35 U.S.C. 154(b) by 0 days.

(21) Appl. No.: 15/121,836

(22) PCT Filed: Mar. 2, 2015

(86) PCT No.: PCT/EP2015/054248
§ 371 (c)(1),
(2) Date: Aug. 26, 2016

(87) PCT Pub. No.: WO2015/128504
PCT Pub. Date: Sep. 3, 2015

(65) Prior Publication Data
US 2017/0057936 A1  Mar. 2, 2017

(30) Foreign Application Priority Data
Feb. 28, 2014 (FR) ..................................... 14 51623

(51) Int. Cl.
C07C 269/04 (2006.01)
C07C 227/04 (2006.01)
C07C 227/16 (2006.01)
C07C 227/18 (2006.01)
C07D 263/06 (2006.01)

(52) U.S. Cl.
CPC .......... C07D 263/06 (2013.01); C07C 227/04 (2013.01); C07C 227/16 (2013.01); C07C 227/18 (2013.01); C07C 269/04 (2013.01)

(58) Field of Classification Search
None
See application file for complete search history.

(56) References Cited

FOREIGN PATENT DOCUMENTS

WO          01/38500 A2     5/2001

OTHER PUBLICATIONS

"Protective Groups in Organic synthesis", (John Wiley & Sons, New York (1981)) Part 1.
"Protective Groups in Organic synthesis", (John Wiley & Sons, New York (1981)) Part 2.
Alessia Amore et al: "Development of a Hypersensitive Periodate-Cleavable Amino Acid that is Methionine- and Disulfide-Compatible and its Application in MHC Exchange Reagents for T Cell Characterisation", CH EMB IOCH EN, vol. 14, No. I, Jan. 2, 2013 (Jan. 2, 2013), pp. 123-131, XP055147135.
Mariana L. Gutierrez et al: "Serine Hydroxymethyl Transferase fromStreptococcus thermophilus andL- Threonine Aldolase fromEscherichia coli as Stereocomplementary Biocatalysts for the Synthesis of [beta]-Hydroxy-[alpha],[omega]-diamino Acid Derivatives", Chemistry—A European Journal, vol. 14, No. 15, May 19, 2008 (May 19, 2008), pp. 4647-4656, XP055146949.
R. Reiner et al: "Zur Kenntni s des Muscazons. 24. Mitteilung ?ber Inhaltsstoffe von Fliegenpilzen", Helvetica Chimica Acta, vol. 50, No. I, Jan. 1, 1967 (Jan. 1, 1976), pp. 128-136, XP055146942, ISSN: 0018-019X, DOI: 10.1002/hlca.19670500120 p. 129; composes 1,3.8.
Shaw, K. J.; Luly, J. R.; Rapoport, H. J. Org. Chem. 1985, 50, 4515.
Sicher J et al: "Amino Acids and Peptides XXVIII. (Stereospecific) synthesis of three- and", Collection of Czechoslovak Chemical Communications, Institute of Organic Chemistry & Biochemistry, Prague; CZ, vol. 24, Jan. 1, 1959 (Jan. 1, 1959), pp. 3719-3729, XP008172798.
Stepan, A. F.; Nguyen, T . . . T.; Anderson, D.; Liang, H.; Zhanshan, Q.; Magee, T. V. Synlett 2011 , 2499.
Vassilev, V. P.; Uchiyama, T.; Kajimoto, T.; Wong, C.-H. Tetrahedron Lett. 1995, 36, 4081.
Vidal, L.; Calveras, J.; Clapes, P.; Ferrer, P.; Caminal, G. Appl. Microbial. Biotechnol. 2005, 68, 489.

Primary Examiner — Samantha Shterengarts
(74) Attorney, Agent, or Firm — Banner & Witcoff, Ltd.

(57) ABSTRACT

The present invention relates to a process for the synthesis of 2,4-diamino-3(S)-hydroxycarboxylic acid derivatives from 5-hydroxyectoine.

15 Claims, 1 Drawing Sheet

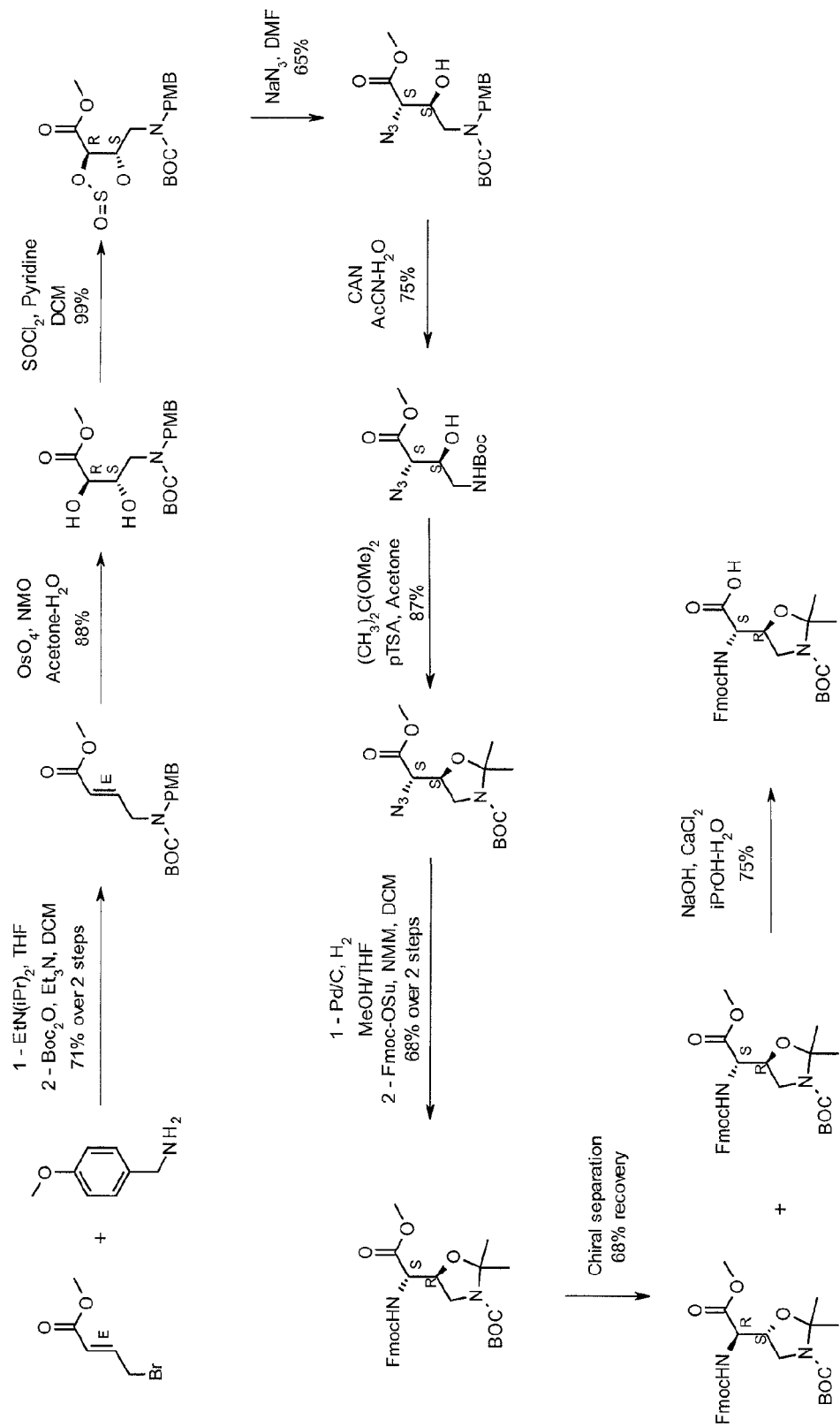

PROCESS FOR PREPARING 2,4-DIAMINO-3-HYDROXYBUTYRIC ACID DERIVATIVES

RELATED APPLICATIONS

This application is a National Stage Application under 35 U.S.C. 371 of co-pending PCT application PCT/EP2015/054248 designating the United States and filed Mar. 2, 2015; which claims the benefit of FR application number 1451623 and filed Feb. 28, 2014 each of which are hereby incorporated by reference in their entireties.

FIELD OF THE INVENTION

The present invention concerns a process to prepare derivatives of 2,4-diamino-3-hydroxybutyric acid.

STATE OF THE ART

The structural similarities between 2,4-diamino-butyric acid, allothreonine and 2(S),4-diamino-3(S)-hydroxybutyric acid means that this latter molecule is of particular interest for use in the pharmaceutical and agrochemical industries and in material sciences. 2(S),4-diamino-3(S)-hydroxybutyric acid and the protected derivatives thereof such as 2(S),4-diamino-3(S)-hydroxybutyric acids having protected primary amine and optionally hydroxy functions, can therefore be of use as building block in the synthesis of various molecules, in particular for the synthesis of novel peptides. It therefore appears desirable to be able to synthesize these compounds on a large scale and at low cost.

At the present time, 2(S),4-diamino-3(S)-hydroxybutyric acid is not commercially available making synthesis of its protected derivatives difficult on an industrial scale. Preparation thereof has been proposed in three steps starting from muscazone (1). It has also been proposed to prepare racemic 2,4-diamino-3-hydroxybutyric acid in nine steps from dicarbomethoxypyrazoline (2). Recently, it has been proposed to prepare the four diastereoisomers of 2,4-diamino-3-hydroxybutyric acid having protected primary amine and hydroxyl functions (herein called "protected 2,4-diamino-3-hydroxybutyric acid") in ten steps (FIG. 1) (3). The proposed synthetic route comprises chiral separation, as second-to-last step, leading to non-negligible product losses. In addition, this synthesis performed on a small scale only led to a few milligrams of the product of interest "protected 2,4-diamino-3-hydroxybutyric acid" with a global molar yield not exceeding 6.4%. Said synthesis cannot realistically be carried out on a large scale.

Other teams have described the synthesis of precursors of protected 2(S),4-diamino-3(S)-hydroxybutyric acid. For example, Wong et al. have described the synthesis via biocatalytic route of (hydroxyl azido) butyric acid by reaction between glycine and an azidoacetaldehyde in the presence of L-threonine aldolase (4). The stereochemistry of the product obtained is said to be (2S, 3S), however the diastereoisomeric ratio is not mentioned. More recently, Clapés et al. have described the reaction between glycine and a protected amino aldehyde in the presence of a serine hydroxymethyltransferase isolated from Streptococcus thermophilus (5). The protected amino hydroxy butyric acid (2S, 3S) was obtained with a molar yield of 13% and modest diastereoisomeric ratio (86:14, 2S, 3S: 2S, 3R). The enzyme used in this process not being commercially available, it must be produced and purified using a complex method making these processes difficult to implement on a large scale. Rapoport et al. prepared precursors of 2(S),4-diamino-3(S)-hydroxybutyric acid in protected form during the total synthesis of complex molecules (6). Epoxidation of 2-amino-3-butenoic acid, obtained in three steps from the methyl ester of L-methionine, led to a mixture of the two diastereoisomers (4:1, 2S, 3S: 2S, 3R). Opening of the 2S, 3S epoxide with an azide ion led to a precursor of protected 2(S),4-diamino-3(S)-hydroxybutyric acid. This method cannot be applied however on a large scale on account of the low stereoselectivity of the epoxidation step and the high number of steps needed to access the compound of interest (8 steps).

There remains a need therefore for the development of a process to prepare protected 2(S),4-diamino-3(S)-hydroxybutyric acid or precursors thereof allowing these to be obtained on a large scale and at low cost.

SUMMARY OF THE INVENTION

The present invention relates to a process to synthesize compounds of following formula (I):

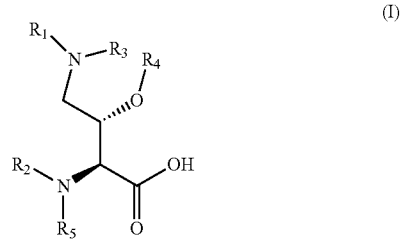

where:
  $R_1$ and $R_2$ independently of each other are protective groups of the amine functions;
  $R_3$ is a hydrogen or a protective group of the amine functions and $R_4$ is a hydrogen or a protective group of the hydroxyl functions, or $R_3$ and $R_4$ together form a group selected from among —C(CH$_3$)$_2$—, —CH(CH$_3$)—, —C((CH$_2$)$_4$)—, —C((CH$_2$)$_5$)—, —CH(CH$_5$)—, —CH((p-OCH$_3$)C$_6$H$_4$)—, —CH((m,p-OCH$_3$)C$_6$H$_3$)— and —C(O)—;
  $R_5$ is a hydrogen, an alkyl radical, aryl radical or heteroaryl radical; from 5-hydroxyectoine.

The present invention also relates to a process to synthesize 2,4-diamino-3(S)-hydroxycarboxylic acid from 5-hydroxyectoine.

FIGURE

The FIGURE illustrates the synthesis scheme for the four diastereoisomers derived from 2,4-diamino-3-hydroxybutyric acid with the primary amine and hydroxyl functions protected according to the prior art.

DETAILED DESCRIPTION OF THE INVENTION

The inventors have developed a process to prepare protected derivatives of 2(S),4-diamino-3(S)-hydroxybutyric acid, from (4S, 5S)-5-hydroxy-2-methyl-1,4,5,6-tetrahydropyrimidine-4-carboxylic acid (2), more commonly known as "5-hydroxyectoine":

(2)

By "protected derivatives of 2(S),4-diamino-3(S)-hydroxy butyric acid" in the description of the present invention is meant a 2(S),4-diamino-3(S)-hydroxybutyric acid of which the primary amine and optionally the hydroxy functions are protected by adapted protective groups. The protected derivatives of 2(S),4-diamino-3(S)-hydroxy butyric acid may be N-substituted at position 2. The protected derivatives of 2(S),4-diamino-3(S)-hydroxy butyric acid are represented by following formula (I):

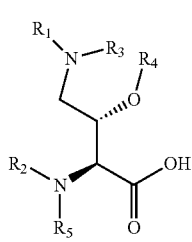

(I)

where:
  $R_1$ and $R_2$ independently of each other are protective groups of the amine functions;
  $R_3$ is a hydrogen or a protective group of the amine functions and $R_4$ is a hydrogen or a protective group of the hydroxyl functions, or $R_3$ and $R_4$ together form a group selected from among —C(CH$_3$)$_2$—, —CH(CH$_3$)—, —((CH$_2$)$_4$)—, —C((CH$_2$)$_5$)—, —CH(C$_6$H$_5$)—, —CH((p-OCH$_3$)C$_6$H$_4$)—, —CH((m,p-OCH$_3$)C$_6$H$_3$)— and —C(O)—;
  $R_5$ is a hydrogen, an alkyl radical, aryl radical or heteroaryl radical.

In above formula (I), $R_1$ and $R_2$ may be the same or different. When the compounds of formula (I) are used in peptide synthesis, $R_1$ and $R_2$ are preferably different.

The protective groups of the primary or secondary amine functions are well known to persons skilled in the art. These groups protect the amine functions of undesirable reactions. For example, a chemical reaction can be performed selectively at another reactive site which is not protected. The protective groups of the amine functions can be such as those described in "Protective Groups In Organic synthesis", (John Wiley & Sons, New York (1981)) and Harrison et al. "Compendium of Synthetic Organic Methods", Vols. 1 to 8 (J. Wiley & Sons, 1971 to 1996). The protective groups of amine functions comprise carbamates, amides, amino acetal derivatives, N-benzyl derivatives, imine derivatives and N-heteroatom derivatives. In particular, $R_1$ and $R_2$ can be selected from among acetyl, benzoyl, pivaloyl, phenylsulfonyl, benzyl (Bn), t-butyloxycarbonyl (Boc), benzyloxycarbonyl (Cbz), p-methoxybenzyloxycarbonyl, p-nitrobenzyl-oxycarbonyl, trichloroethoxycarbonyl (TROC), allyloxycarbonyl (Alloc), 9-Fluorenylmethyloxycarbonyl (Fmoc), trifluoro-acetyl and benzyl carbamates (substituted or unsubstituted) and the like. Preferably, in above formula (I) $R_1$ is a Boc group and $R_2$ is a Fmoc group.

The protective groups of hydroxyl functions are well known to those skilled in the art. These groups protect the hydroxyl functions against undesirable reactions. The protective groups of hydroxyl functions can be such as described in Greene, "Protective Groups In Organic synthesis", (John Wiley & Sons, New York (1981)) and Harrison et al. "Compendium of Synthetic Organic Methods", Vols. 1 to 8 (J. Wiley & Sons, 1971 to 1996). The protective groups of hydroxyl functions comprise substituted or unsubstituted methyl or alkyl ethers or esters e.g. methoxymethyl, benzyloxymethyl, 2-methoxyethoxymethyl, 2-(trimethylsilyl)ethoxymethyl, t-butyl, benzyl and triphenylmethyl, benzyl ethers (substituted or unsubstituted), tetrahydropyranyl ethers, allyl ethers, substituted ethyl ethers e.g. 2,2,2-trichloroethyl, silyl ethers or alkylsilyl ethers, e.g. trimethylsilyl, t-butyldimethylsilyl and t-butyldiphenylsilyl, heterocycle ethers; and esters prepared by reaction of the hydroxyl group with a carboxylic acid e.g. tert-butyl, benzyl or methyl esters, carbonates in particular benzyl or halogenoalkyl carbonate, acetate, propionate, benzoate and the like.

The term "alkyl" designates straight-chain or branched saturated hydrocarbon chains having 1 to 20 carbon atoms, preferably 1 to 12 atoms, even 1 to 6 carbon atoms. Examples of alkyl radicals include the radicals: methyl, ethyl, n-propyl, isopropyl, n-butyl, iso-butyl, sec-butyl and tert-butyl.

The term "aryl" designates an aromatic monocycle or polycyclic system having at least one aromatic ring fused with at least one other ring which may be aromatic or non-aromatic. Aryl radicals may comprise 5 to 10 carbon atoms. The aryl radical may be a phenyl.

The term "heteroaryl" designates an aryl such as defined above in which one or more carbon atoms are replaced by a heteroatom, such as a nitrogen, sulfur or oxygen atom.

The letters "p" and "m" respectively designate the "para" and "meta" positions of a phenyl radical. The letters "p,m" indicate that the phenyl radical is substituted at para and meta position.

Unless otherwise indicated, the reactions described below are conducted at ambient pressure and the indicated reaction yields are molar yields.

The expression "ambient temperature" designates a temperature ranging from 18° C. to 25° C.

The processes developed by the inventors are adapted for preparation on an industrial scale of the protected derivatives of 2(S),4-diamino-3(S)-hydroxybutyric acid through their numerous advantages:
  the derivatives of 2(S),4-diamino-3(S)-hydroxybutyric acid are obtained in a limited number of steps from a commercially available reagent that is relatively low cost: 5-hydroxyectoine;
  the synthetic route does not require chiral synthesis since the chiral centres are contained in the starting reagent;
  the operating conditions are mild;
  only one purification step is needed;
  the product is obtained with high chiral purity (dr>95:5);
  the global yield of the reaction leading to the formula (I) compounds, wherein $R_1$, $R_2$, $R_3$ and $R_4$ are such as defined above and $R_5$ is a hydrogen, is in the order of 21%.

Process to Prepare Protected Derivatives of 2,4-Diamino-3-Hydroxy Butyric Acid

The process to prepare compounds of following formula (I):

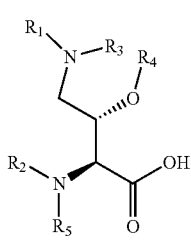

where:
- $R_1$ and $R_2$ independently of each other are protective groups of the amine functions;
- $R_3$ is a hydrogen or protective group of the amine functions and $R_4$ is a hydrogen or protective group of the hydroxyl functions, or $R_3$ and $R_4$ together form a group selected from among —C(CH$_3$)—, —CH(CH)—, —C((CH$_2$)$_4$)—, —C((CH$_2$)$_5$)—, —CH(C$_6$H$_5$)—, —CH((p-OCH$_3$)C$_6$H$_4$)—, —CH((m,p-OCH$_3$)C$_6$H$_3$)— and —C(O)—;
- $R_5$ is a hydrogen, an alkyl radical, aryl radical or heteroaryl radical;

advantageously comprises the following steps:

(a) base hydrolysis of hydroxyectoine and deacetylation leading to 2,4-diamino-3(S)-hydroxybutyric acid;

(b) regioselective protection by an $R_1$ group of the primary amine function at position 4 of the 2,4-diamino-3(S)-hydroxybutyric acid obtained at step (a);

(c) protection by an $R_2$ group of the primary amine function at position 2 of the acid obtained at step (b);

(d) optionally, protection of the hydroxyl function at position 3 by an $R_4$ group and/or protection of the secondary amine at position 4 by an $R_3$ group of the compound obtained at step (c) or protection of the hydroxyl function at position 3 and secondary amine function at position 4 to obtain a compound of formula (I) wherein $R_3$ and $R_4$ together form a group selected from among —C(CH$_3$)$_2$—, —CH(CH$_3$)—, —C((CH$_2$)$_4$)—, —C((CH$_2$)$_5$)—, —CH(C$_6$H$_5$)—, —CH((p-OCH$_3$)C$_6$H$_4$)—, —CH((m,p-OCH$_3$)C$_6$H$_3$)— and —C(O)—;

(e) optionally, N-alkylation or N-arylation at position 2 of the compound obtained at step (d) to obtain a compound of formula (I) wherein $R_5$ is an alkyl group or aryl or heteroaryl group;

(f) recovery of the formula (I) compound obtained at step (c) or, when applicable, at step (d) or (e).

Steps (a), (b), (c), (d) and (e) can be such as described in detail below.

Base Hydrolysis of Hydroxyectoine and Deacetylation (Step (a))

Base hydrolysis and deacetylation can be performed in one single or two steps to lead to 2,4-diamino-3(S)-hydroxybutyric acid (3):

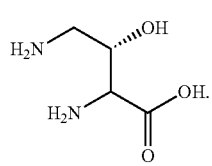

2,4-diamino-3(S)-hydroxy butyric acid is typically obtained with a diastereoisomeric ratio (2S,3S:2R,3S) of at least 70:30. The conversion is quantitative (LC-MS analysis).

Hydrolysis and Deacetylation in Two Steps

Base hydrolysis of hydroxyectoine (opening of hydroxyectoine ring by base hydrolysis) can be obtained by heating to a temperature of 50° C. or higher for at least 3 h30 in the presence of at least one molar equivalent, preferably one to two equivalents, of a strong base such as sodium hydroxide, potassium hydroxide, lithium hydroxide barium hydroxide. Preferably, hydrolysis is conducted in the presence of two molar equivalents of sodium hydroxide at a temperature of 50° C. for five hours. Base hydrolysis is typically performed in a solely aqueous medium.

Base hydrolysis under said conditions leads to opening of the hydroxyectoine ring producing a monoacetylated derivative. The intermediate obtained is then deacetylated via acid hydrolysis e.g. in the presence of hydrochloric acid, sulfuric acid, nitric acid, hydriodic acid, hydrofluoric acid, perchloric acid or hydrobromic acid, by heating to a temperature of at least 95° C. for at least 1 hour. Acid hydrolysis can be conducted in one or more steps as a function of the concentrations involved. For example, if needed, first an acid hydrolysis can be carried out, followed by removal of water and then a second hydrolysis.

Deacetylation is preferably conducted in the presence of 12 N concentrated hydrochloric acid at a temperature of at least 100° C. for 1 hour. Deacetylation is typically performed directly on the crude obtained after the base hydrolysis step.

Base hydrolysis performed in the presence of two molar equivalents of sodium hydroxide at a temperature of 50° C. for five hours, followed by deacetylation via acid hydrolysis in the presence of 12 N concentrated hydrochloric acid at a temperature of at least 100° C. for 1 hour, leads to 2(S),4-diamino-3(S)-hydroxybutyric acid with a diastereoisomeric ratio (2S,3S:2R,3S) of 70:30.

Hydrolysis and Deacetylation in One Step

Alternatively, base hydrolysis of hydroxyectoine (opening of hydroxyectoine ring via base hydrolysis) and deacetylation can be conducted in a single step by heating to a temperature of 85° C. or higher for at least 18 h in the presence of at least seven molar equivalents of a strong base. The strong bases may be those described above. The reaction is typically conducted in an exclusively aqueous medium.

The base hydrolysis of hydroxyectoine (opening of hydroxyectoine ring via base hydrolysis) and deacetylation allow the easy obtaining of 2,4-diamino-3(S)-hydroxycarboxylic acid. Therefore, according to one aspect, the present invention also pertains to a process to synthesise 2,4-diamino-3(S)-hydroxycarboxylic acid from 5-hydroxyectoine. The process comprises base hydrolysis of hydroxyectoine (opening of hydroxyectoine ring via base hydrolysis) and deacetylation leading to 2,4-diamino-3(S)-hydroxybutyric acid. Base hydrolysis and deacetylation are such as described above. 2,4-diamino-3(S)-hydroxycarboxylic acid is obtained in the form of a mixture of diastereoisomers: 2(S),4-diamino-3(S)-hydroxycarboxylic acid and 2(R),4-diamino-3(S)-hydroxycarboxylic acid. The compounds obtained can be separated using methods well-known to skilled persons e.g. chromatography.

Regioselective Protection of the Primary Amine Function at Position 4 (Step (b))

Regioselective protection of the primary amine function at position 4 of the 2,4-diamino-3(S)-hydroxybutyric acid (3) obtained at step (a) can be performed in several suitable manners. It leads to formula (I) compounds wherein $R_2$, $R_3$, $R_4$ and $R_5$ are hydrogen atoms and $R_1$ is a protective group of the amine functions i.e. compounds of formula (Ia):

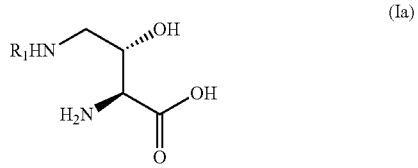

(Ia)

wherein $R_1$ is such as defined above.

In some embodiments, regioselective protection can be carried out in three stages.

At a first stage, a copper complex is prepared by placing the 2,4-diamino-3(S)-hydroxybutyric acid obtained at step (a) in the presence of a copper complex such as $CuSO_4 \cdot 5H_2O$, $CuSO_4$, $Cu_2(OH)_2CO_3$, $Cu(OAc)_2$ or $CuCO_3$. The reaction is typically performed in water under reflux or ambient temperature. Complexing allows simultaneous protection of the carbonyl function and primary amine function at position 2 of the compound obtained at step (a). Preferably, a copper complex is prepared using copper sulfate pentahydrate.

At a second stage, the primary amine function at position 4 is protected by an adapted $R_1$ protective group. For example, the primary amine function at position 4 can be protected by a t-butoxycarbonyl (Boc) or benzyloxycarbonyl group, p-methoxybenzyloxycarbonyl, p-nitrobenzyloxycarbonyl, trichloroethoxycarbonyl (TROC), allyloxycarbonyl (Alloc), 9-Fluorenylmethyloxycarbonyl (Fmoc). Protection by said protective groups can be conducted under conditions well-known to skilled persons. Typically, the reaction is conducted at ambient temperature. Preferably, $R_1$ is a Boc group. The insertion of a Boc protective group is preferably obtained by causing the compound obtained after complexing with copper to react with an anhydride of formula $(Boc)_2O$ or $N_3CO_2tBu/MgO$ in a solvent, such as acetone, water, methanol, ethanol, THF or dioxane.

At a third stage, the copper is decomplexed. The decomplexing of copper can be obtained by reaction with 8-quinolinol or commercially available decomplexing resins (e.g. Chelex 100) or EDTA salts. Typically, the reaction is conducted at ambient temperature. Preferably, decomplexing of the copper is performed with 8-quinolinol, typically in water. This third copper decomplexing stage is optional. Therefore, it is also possible to use the copper complex obtained directly in the remainder of the process.

Surprisingly, the 2,4-diamino-3-hydroxybutyric acid protected at position 4 of (2S, 3S) configuration, or its copper complex, is obtained after these steps with diastereoisomeric purity higher than 90%, preferably higher than 95%.

Alternatively, the regioselective protection of the primary amine function at position 4 of the 2,4-diamino-3(S)-hydroxybutyric acid obtained at step (a) can be performed by complexing the 9-BBN boron atom with the amine function at position 2 and the acid function. This complexing provides temporary protection of the amine function at position 2. At a second stage, the primary amine function at position 4 is protected by a Boc protective group. The reaction conditions of the protection reaction are well-known to those skilled in the art. Typically, the reaction is conducted at ambient temperature. For example, the primary amine function at position 4 is protected by a Boc protective group via reaction of the complex obtained, under base conditions, with $Boc_2O$. The boron is then decomplexed in the presence of ethylenediamine.

In some embodiments, regioselective protection of the primary amine function at position 4 of the 2,4-diamino-3 (S)-hydroxybutyric acid obtained at step (a) can be obtained by reaction with sodium hydroxide and $(Boc)_2O$ or $N_3CO_2tBu$ or 1H-benzotriazole, with DMAP and $Boc_2O$ or $PhOCO_2tBu$, typically at ambient temperature.

When regioselective protection of the primary amine function at position 4 is obtained with a Boc group, following compound (4), or the copper complex thereof $(4)_2Cu$, is obtained:

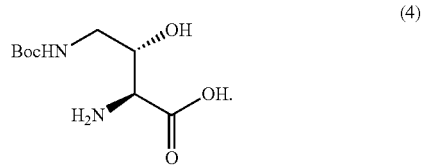 [SMILES: CC(C)(C)OC(=O)NC[C@H](O)[C@H](N)C(=O)O]

(4)

Protection of the Primary Amine Function at Position 2 (Step (c))

The primary amine function at position 2 is protected by an adapted $R_2$ protective group. This step leads to formula (I) compounds wherein $R_3$, $R_4$ and $R_5$ are hydrogen atoms i.e. to the following compounds of formula (Ib):

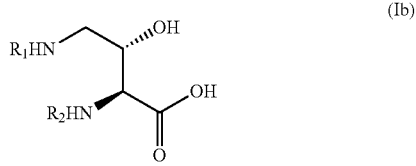

(Ib)

where $R_1$ and $R_2$ are such as defined above.

The $R_2$ group may be a t-butoxycarbonyl (Boc), benzyloxycarbonyl, p-methoxybenzyloxycarbonyl, p-nitrobenzyloxycarbonyl, trichloroethoxycarbonyl (TROC), allyloxycarbonyl (Alloc) or 9-Fluorenylmethyloxycarbonyl (Fmoc) group.

The protection of the primary amine function at position 2 is preferably obtained with a 9-fluorenylmethoxycarbonyl group (Fmoc). The insertion of a Fmoc group can be performed under conditions well-known to persons skilled in the art e.g. by reaction of the product obtained at step (b) with 9-fluorenyl-methoxycarbonyl hydroxy succinimide (FmocOSu) in the presence of a solvent such as dioxane, typically at ambient temperature.

When $R_1$ is a Boc group and $R_2$ a Fmoc group, following compound (5) is obtained:

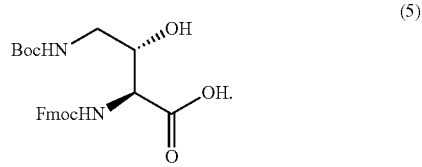

(5)

The formula (Ib) compound obtained after this step can be collected. It can be purified by silica gel column chromatography with Heptane/ethyl acetate gradient of 100:0 to 0:100 (volume/volume). The product is obtained with a yield of 30% over the first four steps.

Diastereoisomeric purity higher than 90%, preferably higher than 95% is obtained.

The formula (Ib) compound obtained after this step (c) can optionally be subjected to step (d) and optionally step (e) described below, before or after purification.

Protection of the Hydroxyl Function at Position 3 and Secondary Amine Function at Position 4 (Step (d))

Protection of the hydroxyl function at position 3 and/or of the secondary amine function at position 4 can be obtained using adapted protective groups and leads to the formula (I) compounds wherein $R_1$ and $R_2$ are such as defined above, $R_5$ is a hydrogen, $R_3$ is a hydrogen or protective group of the amine functions and $R_4$ is a hydrogen or protective group of the hydroxyl functions, or $R_3$ and $R_4$ together form a group selected from among —C(CH$_3$)$_2$—, —CH(CH$_3$)—, —C((CH$_2$)$_4$)— —C((CH$_2$)$_5$)—, —CH(C$_6$H$_5$)—, —CH((p-OCH$_3$)CH$_4$)—, —CH((m,p-OCH$_3$)C$_6$H$_3$)— and —C(O)—, i.e. compounds of following formula (Ic):

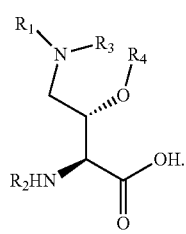

(Ic)

In some embodiments, the protection of the hydroxyl function at position 3 and of the secondary amine function at position 4 is performed using isopropylidene leading to compounds of formula (I) such as described above wherein $R_3$ and $R_4$ together form a —C(CH$_3$)$_2$— group, i.e. leading to compounds of following formula (Id):

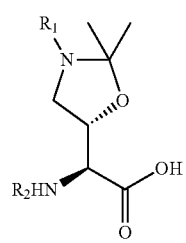

(Id)

wherein $R_1$ and $R_2$ are such as described above.

The reaction between the compound of formula (Ib) obtained after step (c) and 2,2'-dimethoxy propane is typically conducted in dichloromethane in the presence of BF$_3$.OEt$_2$, preferably at 0° C.

When $R_1$ is a Boc group and $R_2$ a Fmoc group, following compound (1) is obtained:

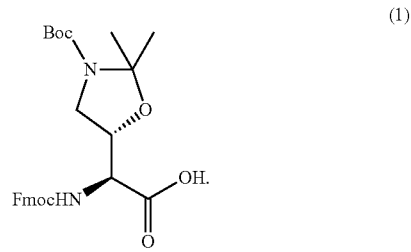

(1)

The compound is obtained after this step with diastereoisomeric purity higher than 90%, preferably higher than 95%. The reaction yield is 70%.

The compound obtained can then be purified by recrystallization.

N-Alkylation or N-Arylation at Position 2 (Step (e))

The synthesis of N-substituted derivatives can be performed in three steps starting from the compound obtained at step (d): esterification of the acid function, N-substitution (N-alkylation or N-arylation) of the free carbamate function and chemoselective saponification of the ester function in the presence of the Fmoc group.

The reactions are conducted under conditions well known to skilled persons.

The first esterification step takes place in the presence of an alcohol and coupling agent.

N-substitution on the free carbamate function can be of two types:
  N-alkylation in the presence of an RX alkylating agent such as an alkyl halide, alkyl sulfonate, optionally of a base (different from a secondary amine) and optionally of a solvent (different from a secondary amine and an alcohol).
  N-arylation in the presence of an aromatic or heteroaromatic ring carrying a function enabling it to react in couplings catalysed by metals (halides, sulfonate, diazonium.) and of a catalyst system (a metal optionally with a ligand, optionally a base and optionally a solvent).

Saponification of the ester function in the presence of the protective Fmoc group is performed selectively, preferably in the presence of NaOH and CaCl$_2$, or in the presence of LiI or Me$_3$SnOH.

In particular, the N-substituted derivatives can be obtained using the following synthesis scheme:

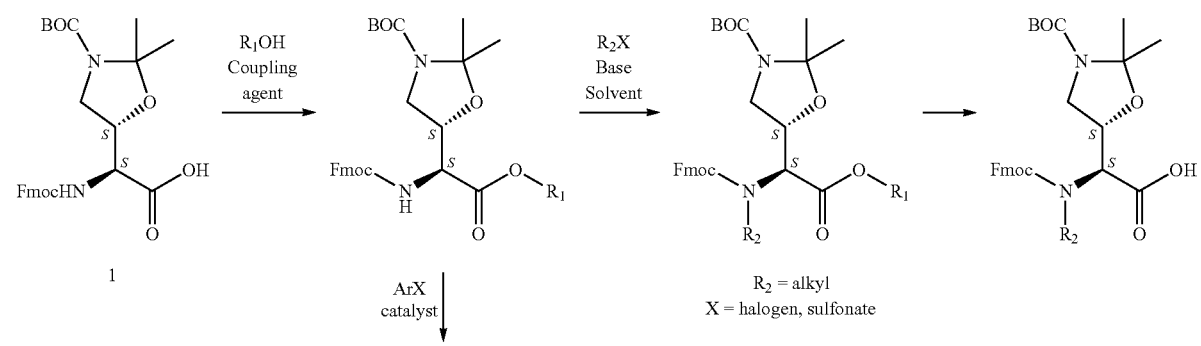

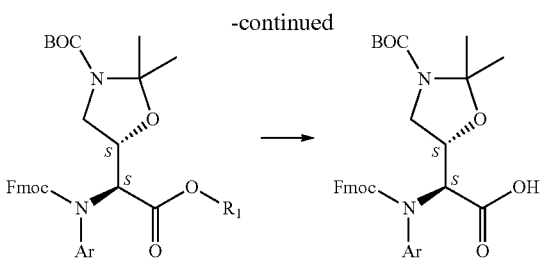

The compounds obtained after step (d) and optionally (e) are collected. They can be purified using methods well known to those skilled in the art.

In one embodiment of the present invention, protected derivatives of 2,4-diamino-3-hydroxy butyric acid are prepared with the following synthesis scheme:

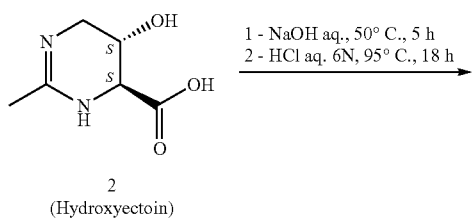

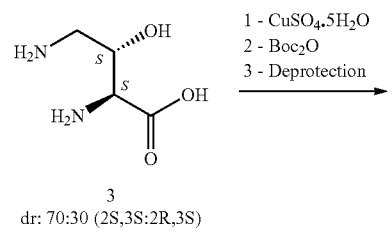

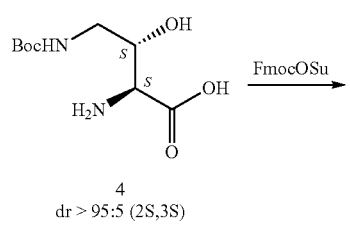

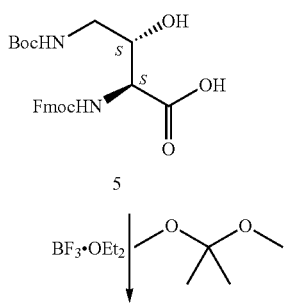

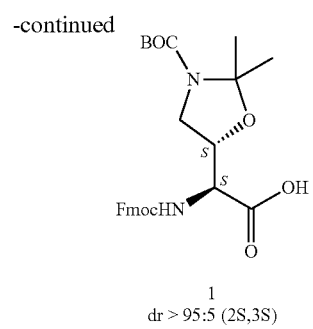

The desired product (1) is obtained with a global yield in the order of 21% and with chiral purity higher than 95%.

EXAMPLES

Example 1

Preparation of Compound (3)

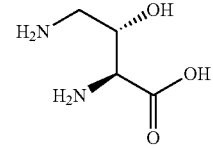

10 g of hydroxyectoine (63.2 mmol) is dissolved in 200 mL of water and 5.1 g of sodium hydroxide (2.0 equiv., 126.6 mmol) are added. The solution is left under agitation at 50° C. for hours.

LC-MS analysis of the reaction mixture shows disappearance of the starting reagent and the onset of a new compound ([M+H$^+$]=177) corresponding to a monoacetylated intermediate.

The solution is cooled to 0° C. and concentrated hydrochloric acid added up to a pH of 1 (~50 mL). The solution is then heated at 95° C. for 18 hours.

LC-MS analysis of the reaction mixture showed the disappearance of the monoacetylated intermediate and the formation of 2,4-diamino-3-hydroxybutyric acid 3 ([M+H$^+$]=135).

The solution is concentrated to give a pale yellow solid (20.8 g).

Marfey analysis of this sample shows that it is a mixture of two diastereoisomers (2S, 3S/2R, 3S=70:30).

Preparation of Compound (4)

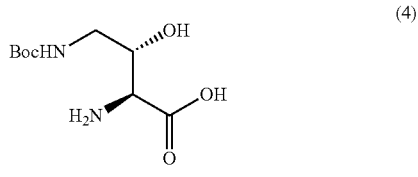 [SMILES: CC(C)(C)OC(=O)NC[C@H](O)[C@H](N)C(=O)O]

The pale yellow solid obtained at the preceding step is dissolved in 60 mL of water. The solution obtained is cooled to 0° C. and sodium bicarbonate (2.0 equiv., 10.6 g, 126.4 mmol) then added portion-wise. A solution of $CuSO_4.5H_2O$ (0.5 equiv., 7.9 g, 31.6 mmol) in water (20 mL) is added dropwise to the preceding solution. The green solution obtained is left under agitation at ambient temperature for 18 hours. The solution is then cooled to 0° C. Thereafter, sodium bicarbonate (2.0 equiv., 10.6 g, 126.4 mmol) is added portion-wise. Once the solution has reached ambient temperature, a solution of di-tert-butyl dicarbonate (1.3 equiv., 17.9 g, 82.2 mmol) in acetone (20 mL) is added dropwise. The thick green solution obtained is left under agitation at ambient temperature for 18 hours. 100 mL of methanol are subsequently added and the mixture agitated for 6 hours. The blue suspension obtained is filtered. A blue solid is collected (15.2 g).

The solid is placed in suspension in 500 mL water and 22 g of 8-quinolinol (2.5 equiv., 22.0 g, 156.0 mmol) added thereto. The mixture is left under agitation at ambient temperature for 18 hours and filtered. The collected solid is rinsed in water (50 mL) and the collected waters analysed by LC-MS. The formation of a new compound was evidenced ($[M+H^+]=235$).

The solution is concentrated in vacuo to give compound 4 in the form of a pale brown solid (30.1 g).

Marfey analysis of this sample reveals the presence of a single diastereoisomer (2S, 3S, dr>95:5).

Preparation of Compound (5)

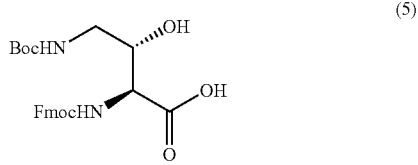

30.1 g of the compound obtained at the preceding step are dissolved in 1.5 L water. The solution is cooled to 0° C. Sodium bicarbonate (2.0 equiv., 10.5 g, 125.6 mmol) is slowly gently added. Once the solution has reached ambient temperature, a solution of FmocOSu (1.1 equiv., 23.2 g, 69.0 mmol) in dioxane (200 ml) is added dropwise under rapid agitation. A white solid is obtained. The suspension is left under agitation at ambient temperature for 18 hours. After this time, the suspension is filtered and the filtrate concentrated in vacuo to give the compound in the form of a pale brown solid (22.0 g) (LC-MS: $[M+H^+]=457$).

The compound is purified on a silica gel chromatographic column (Heptane/ethyl acetate 100:0 to 0:100.). Compound 5 is obtained in the form of a white solid (8.6 g, purity: 95% by LC-MS).

Compound 5 is obtained with a global yield of 30% in 4 steps.

Preparation of Compound (1)

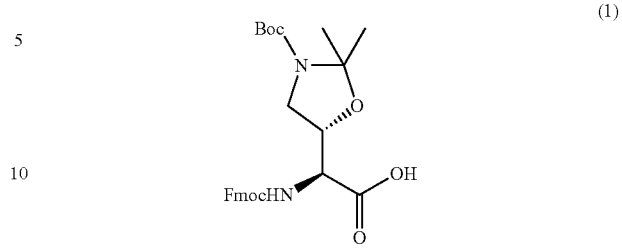

Compound 5 (8.5 g, 18.6 mmol) is dissolved in dichloromethane (300 mL) and 2,2'-dimethoxy propane (300 ml) added thereto. The solution is cooled to 0° C. and 2 mL of $BF_3.OEt_2$ (cat.) then added dropwise. The solution is left at ambient temperature and under agitation for 18 hours.

The reaction mixture is washed with sodium bicarbonate saturated aqueous solution. The aqueous and organic layers are separated. The organic layer is dried over magnesium sulfate, filtered and concentrated in vacuo to give a pale yellow oil. This oil is triturated with heptane to give compound 1 in the form of a white solid (6.5 g, 95% purity by LC-MS, 70% yield).

Marfey analysis of this sample reveals the presence of the expected diastereoisomer (2S, 3S, dr>95:5).

The global yield over the 5 steps of this synthesis is 21%.

Example 2

The process of the present invention can also be applied in the presence of higher amounts of reagents.

Preparation of Compound (3)

Hydroxyectoine (50.0 g, 316.4 mmol) was dissolved in water (260 mL). NaOH (2.0 equiv., 632.9 mmol, 25.3 g) was added portion-wise and the mixture was agitated at ambient temperature until total NaOH dissolution. The solution obtained was heated at 50° C. for 6 h, cooled to ambient temperature and then to 5° C. using an ice bath. Aqueous HCl (6 N) was slowly added (~100 mL) until obtaining of a solution at pH=4. The solution obtained was frozen to −80° C. and lyophilised. The white solid obtained was dissolved in aqueous HCl (6 N, 300 mL) and the mixture heated to 110° C. for 3 hours (LC-MS analysis showed the expected product and a few impurities). The solution obtained was diluted with water (300 mL), frozen to −80° C. and lyophilised to give (3) in the form of a pale yellow solid (107 g, containing 2.0 equiv. of NaCl, purity >90% with LC-MS, Marfey analysis showed a mixture of two diastereoisomers (2S,3S/2R,3S=70:30).

LC-MS: Rt=2.30 min, $[M+H]^+=135$ $^1H$ NMR ($D_2O$, 600 MHz, mixture of 2 diastereoisomers 70:30): d 3.22 (dd, J=10.2 and 13.2 Hz, 0.3H); 3.34-3.47 (m, 1.7H); 4.08 (d, J=4.8 Hz, 0.3H); 4.24 (d, J=3.0 Hz, 0.7H); 4.46 (td, J=3.0 and 10.2 Hz, 0.7H); 4.48-4.52 (m, 0.3H).

$^{13}C$ NMR ($D_2O$, 150 MHz, mixture of 2 diastereoisomers): d 42.65; 43.38; 57.70; 66.92; 67.45; 170.45.

Marfey analysis: 2S,3S/2R,3S=73:27 (2S,3S: Rt=96.01 min, 73%; 2R,3S: Rt=97.84 min, 27%)

Preparation of Compound $(4)_2Cu$

The mixture of the two diastereoisomers obtained at the preceding step for the preparation of (2S,3S)-2,4-diamino-3-hydroxy-butanoic acid (3) (53 g, ~160 mmol) was placed in a 2 L round-bottom flask and dissolved in water (250 mL). NaOH (3.0 equiv., 480 mmol, 19.0 g) was added portion-wise. The mixture was agitated until dissolution of the solids and a solution of $CuSO_4.5H_2O$ (0.5 equiv., 80 mmol, 20.0 g) in water (125 mL) was slowly added. The dark blue solution obtained was placed in an oil bath at ambient temperature. The system was heated from 25 to 110° C. (in 25 minutes) left at 110° C. for 30 minutes and then cooled to ambient temperature for 4 hours. A solution of $Boc_2O$ (2.0 equiv., 320 mmol, 52.0 g) in dioxane (275 mL) was added and the reaction left under agitation at ambient temperature for 70 hours. A solution of $Boc_2O$ (0.5 equiv., 80 mmol, 13.0 g) in dioxane (60 mL) was slowly added and the mixture left under agitation at ambient temperature for 24 hours. The suspension obtained was filtered. The pale blue solid obtained was rinsed in water (~700 mL), diethyl ether (~300 mL) and dried to give ((2S,3S)-2-amino-4-(tert-butoxycarbonylamino)-3-hydroxy-butanoic acid)$_2$Cu in the form of a pale blue solid (17.1 g, 40% yield in two steps).

Preparation of Compound (5)

Next, the ((2S,3S)-2-amino-4-(tert-butoxycarbonylamino)-3-hydroxy-butanoic acid)$_2$Cu previously obtained (17.1 g, 32.0 mmol) was suspended in water (300 mL). A solution of $Na_2EDTA$ (1.5 equiv., 48.0 mmol, 15.9 g) and NaOH (3.0 equiv., 96.0 mmol, 3.84 g) in water (300 mL) was added. The mixture was left under agitation at ambient temperature for 4 hours until complete dissolution of the suspension. The solution obtained was cooled over an ice bath and a solution of FmocOSu (2.5 equiv., 80.0 mmol, 35.7 g) in dioxane (500 mL) gently added. On completion of the addition, $Na_2CO_3$ (2.5 equiv., 80.0 mmol, 8.5 g) was added and the mixture heated to ambient temperature for 18 hours. The clear blue solution obtained was washed in diethyl ether (4*200 mL) then cooled over an ice bath. 1 N aqueous HCl was slowly added until a solution at pH=3-4 (~250 mL) was obtained. This aqueous phase was extracted with ethyl acetate (5*200 mL). The organic phases were combined, washed with saturated NaCl aqueous solution (2*150 mL), dried over $MgSO_4$, filtered and concentrated to give a pale yellow oil. Acetonitrile (200 mL) was added and the mixture left under agitation at ambient temperature for 70 hours. The suspension was filtered, the solid rinsed with acetonitrile (100 mL) and dried to give (5) in the form of a white powder (29.1 g, quantitative yield, 95% purity by LC-MS). Marfey analysis of this sample revealed the presence of a single diastereoisomer (2S, 3S, dr>95:5).

LC-MS: Rt=13.96 min, 95% (254 nm), [M+H-Boc]$^+$=357

$^1$H NMR (DMSO-de, 600 MHz, 343 K): d 1.39 (s, 9H); 3.00-3.04 (m, 1H); 3.12-3.20 (m, 1H); 3.85-3.88 (m, 1H); 4.00-4.13 (m, 1H); 4.22-4.25 (m, 1H); 4.28-4.31 (m, 2H); 6.61 (br s, 0.8H); 7.33 (t, J=7.2 Hz, 2H); 7.42 (t, J=7.2 Hz, 2H); 7.71 (d, J=7.2 Hz, 2H); 7.87 (d, J=7.2 Hz, 2H).

$^{13}$C NMR (DMSO-de, 150 MHz, 343 K): d 27.93; 42.88; 46.48; 57.26; 65.69; 69.96; 77.56; 119.65; 124.87; 126.70; 127.24; 140.40; 143.50; 143.54; 151.30; 155.41; 155.65; 171.06. Marfey analysis: Rt=95.60 min (2S, 3S), 100% (340 nm), [M+H]$^+$=695.15

Preparation of Compound (1)

(2S,3S)-4-(tert-butoxycarbonylamino)-2-(9H-fluoren-9-ylmethoxycarbonylamino)-3-hydroxy-butanoic acid (5) (29.1 g, 63.6 mmol) was suspended in a mixture of acetone and 2,2-dimethoxypropane (1:1, 480 mL). The suspension was cooled over an ice bath and $BF_3.OEt_2$ (catalytic, 900 µL) was added dropwise. The reaction was agitated in the ice bath until an orange/brown solution was obtained. Aqueous $NaHCO_3$ saturated solution (200 mL) was added. The aqueous phase was extracted with ethyl acetate (2*200 mL). The organic phases were combined, washed with aqueous 0.1 N HCl solution (200 mL) and aqueous NaCl saturated solution (200 mL), dried over $MgSO_4$, filtered and concentrated. The pale yellow oil obtained was dissolved in diethyl ether (100 mL) and the solution cooled over an ice bath after which hexane (400 mL) was added. When adding hexane the formation of solids was observed. On completion of the addition, the presence of a tacky solid at the bottom of the round-bottom flask was observed. Diethyl ether was added at ambient temperature and the mixture triturated until a white solid was obtained which was then triturated for 18 hours. The suspension obtained was filtered to give (1) in the form of a white powder (22.9 g, 73% yield, 96% purity by LC-MS).

LC-MS: Rt=19.66 min, 96% (254 nm), [M+H-Boc-CH(CH$_3$)$_2$]$^+$=357

$^1$H NMR (DMSO-d$_6$, 600 MHz, 343 K) d 1.43 (s, 12H), 1.47 (s, 3H), 3.36-3.41 (m, 1H), 3.54-3.59 (m, 1H), 4.22-4.25 (m, 2H), 4.30-4.33 (m, 2H), 4.38 (br s, 1H), 7.30-7.34 (m, 2H), 7.39-7.44 (m, 2H), 7.58 (br s, 1H), 7.69-7.72 (m, 2H), 7.87 (d, J=7.8, 2H).

$^{13}$C NMR (DMSO-d$_6$, 150 MHz, 343 K): d 27.78, 46.48, 46.84, 65.72, 72.81, 78.86, 92.94, 119.65, 124.83, 126.66, 127.25, 140.41, 143.48, 151.04, 155.51, 170.37.

The regioselectivity of the protections was determined using NMR analyses (HMBC and HSQC). A clear signal was observed under HMBC between CHa (4.25 ppm) and CO of Fmoc protecting the amine at position a (155.5 ppm) thereby proving the regioselectivity of the protections.

Marfey analysis: Rt=96.19 min (2S, 3S), 100% (340 nm), [M+H]$^+$=695.15

REFERENCES

1. Reiner, R.; Eugster, C. H. *Helv. Chim. Acta* 1967, 50, 128.
2. Sicher, J.; Rajsner, M.; Rudinger, J; Eckstein, M.; Sorm, F. *Coll. Czech. Chem. Comm;* 1959, 24, 3719.
3. Stepan, A. F.; Nguyen, T.-T.; Anderson, D.; Liang, H.; Zhanshan, Q.; Magee, T. V. *Synlett* 2011, 2499.
4. Vassilev, V. P.; Uchiyama, T.; Kajimoto, T.; Wong, C.-H. *Tetrahedron Lett.* 1995, 36, 4081.
5. Vidal, L.; Calveras, J.; Clapes, P.; Ferrer, P.; Caminal, G. *Appl. Microbiol. Biotechnol.* 2005, 68, 489.
6. Shaw, K. J.; Luly, J. R.; Rapoport, H. *J. Org. Chem.* 1985, 50, 4515.

The invention claimed is:

1. A process to synthesize compounds of following formula (I):

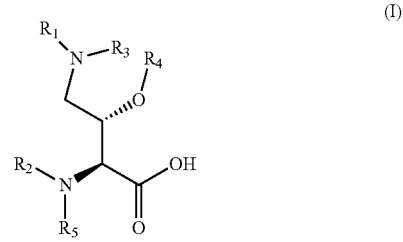

where:
   $R_1$ and $R_2$ independently of each other are protective groups of the amine functions;
   $R_3$ is a hydrogen or a protective group of the amine functions and $R_4$ is a hydrogen or a protective group of the hydroxyl functions, or $R_3$ and $R_4$ together form a group selected from among —C(CH$_3$)$_2$—, —CH(CH$_3$)—, —C((CH$_2$)$_4$)—, —C((CH$_2$)$_5$)—, —CH (C₆H₅)—, —CH((p-OCH₃)C₆H₄)—, —CH((m,p-OCH₃)C₆H₃)— and —C(O)—;

R₅ is a hydrogen, an alkyl radical, aryl radical or heteroaryl radical;

from 5-hydroxyectoine.

2. The synthetic process according to claim 1 comprising the following steps:
(a) base hydrolysis of hydroxyectoine and deacetylation leading to 2,4-diamino-3(S)-hydroxy butyric acid;
(b) regioselective protection by a R₁ group of the primary amine function at position 4 of the 2,4-diamino-3(S)-hydroxybutyric acid obtained at step (a);
(c) protection by an R₂ group of the primary amine function at position 2 of the acid obtained at step (b);
(f) recovering the compound of formula (I) obtained at step (c).

3. The synthesis process according to claim 1 comprising the following steps:
(a) base hydrolysis of hydroxyectoine and deacetylation leading to 2,4-diamino-3(S)-hydroxy butyric acid;
(b) regioselective protection by a R₁ group of the primary amine function at position 4 of the 2,4-diamino-3(S)-hydroxybutyric acid obtained at step (a);
(c) protection by an R₂ group of the primary amine function at position 2 of the acid obtained at step (b);
(d) protection of the hydroxyl function at position 3 by an R₄ group and/or protection of the secondary amine at position 4 by an R₃ group of the compound obtained at step (c) or protection of the hydroxyl function at position 3 and secondary amine function at position 4 to obtain a compound of formula (I) wherein R₃ and R₄ together form a group selected from among —C(CH₃)₂—, —CH(CH₃)—, —C((CH₂)₄)—, —C((CH₂)₅)—, —CH(C₆H₅)—, —CH((p-OCH₃)C₆H₄)—, —CH((m,p-OCH₃)C₆H₃)— and —C(O)—;
(f) recovering the compound of formula (I) obtained at step (d).

4. The synthesis process according to claim 1 comprising the following steps:
(a) base hydrolysis of hydroxyectoine and deacetylation leading to 2,4-diamino-3(S)-hydroxy butyric acid;
(b) regioselective protection by a R₁ group of the primary amine function at position 4 of the 2,4-diamino-3(S)-hydroxybutyric acid obtained at step (a);
(c) protection by an R₂ group of the primary amine function at position 2 of the acid obtained at step (b);
(d) protection of the hydroxyl function at position 3 by an R₄ group and/or protection of the secondary amine at position 4 by an R₃ group of the compound obtained at step (c) or protection of the hydroxyl function at position 3 and secondary amine function at position 4 to obtain a compound of formula (I) wherein R₃ and R₄ together form a group selected from among —C(CH₃)₂—, —CH(CH₃)—, —C((CH₂)₄)—, —C((CH₂)₅)—, —CH(C₆H₅)—, —CH((p-OCH₃)C₆H₄)—, —CH((m,p-OCH₃)C₆H₃)— and —C(O)—;
(e) N-alkylation or N-arylation at position 2 of the compound obtained at step (d) to obtain a compound of formula (I) wherein R₅ is an alkyl radical, aryl radical or heteroaryl radical;
(f) recovering the compound of formula (I) obtained at step (e).

5. The synthesis process according to claim 2, wherein the hydrolysis and deacetylation at step (a) are performed in the presence of at least 7 molar equivalents of a strong base for at least 18 h at a temperature of 85° C. or higher.

6. The synthesis process according to claim 2, wherein the hydrolysis at step (a) is performed in the presence of a least one molar equivalent of a strong base for at least 3 h30 at a temperature of 50° C. or higher, followed by deacetylation via acid hydrolysis at a temperature of at least 95° C. for at least 1 hour.

7. The synthesis process according to claim 2, wherein the regioselective protection of the primary amine function at position 4 at step (b) comprises the following steps:
(b1) preparing a copper complex by placing the 2,4-diamino-3-hydroxybutyric acid obtained at step (a) in the presence of compound selected from among CuSO₄.5H₂O, CuSO₄, Cu₂(OH)₂CO₃, Cu(OAc)₂ and CuCO₃;
(b2) protecting the primary amine function at position 4 by an R₁ group.

8. The synthesis process according to claim 2, wherein the regioselective protection of the primary amine function at position 4 at step (b) comprises the following steps:
(b1) preparing a copper complex by placing the 2,4-diamino-3-hydroxybutyric acid obtained at step (a) in the presence of compound selected from among CuSO₄.5H₂O, CuSO₄, Cu₂(OH)₂CO₃, Cu(OAc)₂ and CuCO₃;
(b2) protecting the primary amine function at position 4 by an R₁ group;
(b3) decomplexing the copper to obtain the compound of following formula:

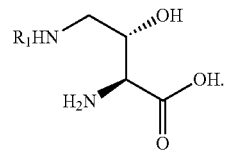

9. The synthesis process according to claim 7, wherein at step (b2) the primary amine function at position 4 is protected by a Boc group.

10. The synthesis process according to claim 2, wherein the protection of the primary amine function at position 2 at step (c) is obtained by reaction with FmocOSu.

11. The synthesis process according to claim 2, wherein the formula (I) compound has the following formula:

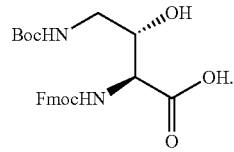

12. The synthesis process according to claim 2, wherein step (d) comprises the reaction of the acid obtained at step (c) with isopropylidene leading to the compound of following formula (Id):

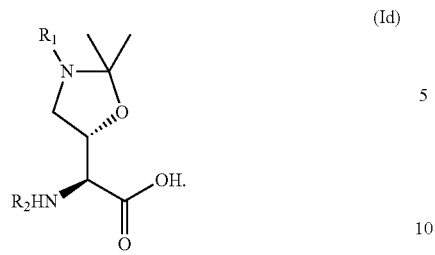

13. The synthesis process according to claim 2, wherein the formula (I) compound is obtained with diastereoisomeric purity higher than 90%.

14. A process to synthesize 2,4-diamino-3(S)-hydroxycarboxylic acid from 5-hydroxyectoine.

15. The process to synthesize 2,4-diamino-3(S)-hydroxycarboxylic acid according to claim 14 comprising base hydrolysis of hydroxyectoine and deacetylation to lead to 2,4-diamino-3(S)-hydroxy butyric acid.

\* \* \* \* \*